US00PP29486P3

(12) United States Plant Patent
Jachertz

(10) Patent No.: US PP29,486 P3
(45) Date of Patent: Jul. 10, 2018

(54) ***GASTERALOE* PLANT NAMED 'D SIGMA'**

(50) Latin Name: *Gasteraloe beguinii*
Varietal Denomination: D Sigma

(71) Applicant: Christian Jachertz, Amposta (ES)

(72) Inventor: Christian Jachertz, Amposta (ES)

(73) Assignee: Deltacactus S.L., Amposta (ES)

( * ) Notice: Subject to any disclaimer, the term of this patent is extended or adjusted under 35 U.S.C. 154(b) by 0 days.

(21) Appl. No.: 15/530,128

(22) Filed: Dec. 5, 2016

(65) Prior Publication Data

US 2018/0160603 P1 Jun. 7, 2018

(51) Int. Cl.
*A01H 5/12* (2018.01)
*A61K 36/886* (2006.01)

(52) U.S. Cl.
USPC ..... Plt./373
CPC ..... *A01H 5/12* (2013.01); *A61K 36/886* (2013.01)

(58) Field of Classification Search
USPC ..... Plt./373
See application file for complete search history.

(56) References Cited

PUBLICATIONS

UPOV-PLUTO: Plant Variety Database, Dec. 13, 2017, citation for 'D Sigma'. 1 page.*

* cited by examiner

*Primary Examiner* — Susan McCormick Ewoldt
*Assistant Examiner* — Karen M Redden

(57) ABSTRACT

A new cultivar of *Gasteraloe* plant named 'D Sigma' that is characterized by a flattened rosette plant shape and green serrated leaves with white dots and white teeth.

1 Drawing Sheet

Botanical classification: *Gasteraloe beguinii.*
Variety denomination: 'D Sigma'.

BACKGROUND OF THE INVENTION

The present invention relates to a new and distinct cultivar of *Gasteraloe* plant botanically known as *Gasteraloe beguinii* and hereinafter referred to by the cultivar name 'D Sigma'.

'D Sigma' was discovered as a naturally occurring whole plant mutation among a population of unnamed *Gasteraloe beguinii* cultivars. The cultivar 'D Sigma' was discovered by the inventor in 2012 in a controlled environment as a single plant in a cultivated area of Amposta, Tarragona, Spain. The parentage of 'D Sigma' is unknown.

Asexual reproduction of the new cultivar 'D Sigma' first occurred by leaf cuttings in 2012 in Amposta, Tarragona, Spain. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Gasteraloe* cultivar 'D Sigma'. These traits in combination distinguish 'D Sigma' as a new and distinct cultivar apart from other existing varieties of *Gasteraloe* known by the inventor.

1. *Gasteraloe* 'D Sigma' exhibits green leaves with large white dots.
2. *Gasteraloe* 'D Sigma' exhibits leaf margins with white teeth.

3. *Gasteraloe* 'D Sigma' exhibits a flattened rosette plant shape.

The closest comparison cultivars are *Gasteraloe* 'Swello' (U.S. Plant Pat. No. 22,012) and Gasteria 'Royal Highness' (not patented). 'D Sigma' is distinguishable from 'Swello' by the following characteristics:

1. *Gasteraloe* 'D Sigma' exhibits a lighter green leaf color than the leaf color of 'Swello'.
2. *Gasteraloe* 'D Sigma' exhibits a dull leaf luster. In comparison, the leaves of 'Swello' are shiny.
3. *Gasteraloe* 'D Sigma' exhibits a flattened open rosette shaped. In comparison, 'Swello' has a more upright closed rosette shape.
4. *Gasteraloe* 'D Sigma' exhibits leaves having larger white dots that are fewer in number than the dots on the leaves of 'Swello'.
5. *Gasteraloe* 'D Sigma' exhibits larger teeth on the leaf margins than the teeth on the leaf margins of 'Swello'.

'D Sigma' is distinguishable from 'Royal Highness' by the following characteristics:

1. *Gasteraloe* 'D Sigma' exhibits a darker green leaf color than the leaf color of 'Royal Highness'.
2. *Gasteraloe* 'D Sigma' exhibits a flattened open rosette shape. In comparison, 'Royal Highness' has a more upright rosette shape.
3. *Gasteraloe* 'D Sigma' exhibits leaves having larger white dots that are fewer in number than the dots on the leaves of 'Royal Highness'. The dots on the leaves of 'Royal Highness' are arranged in stripes.
4. *Gasteraloe* 'D Sigma' exhibits larger teeth on the leaf margins than the teeth on the leaf margins of 'Royal Highness'.

'D Sigma' is distinguishable plants of the species *Gasteraloe beguinii* by the following characteristics:

1. *Gasteraloe* 'D Sigma' exhibits leaves having larger white dots that are fewer in number than the dots on the leaves of plants of the species *Gasteraloe beguinii.*
2. *Gasteraloe* 'D Sigma' exhibits leaves having white dots. In comparison, the dots of plants of the species *Gasteraloe beguinii* are duller white in color.
3. *Gasteraloe* 'D Sigma' exhibits shorter leaves than the leaves of plants of the species *Gasteraloe beguinii.*

BRIEF DESCRIPTION OF THE DRAWING

The accompanying photograph illustrates the distinguishing traits of *Gasteraloe* 'D Sigma'. The photograph shows an overall view of a 12 month old plant. The photograph was taken using conventional techniques and although colors may appear different from actual colors due to light reflectance, it is as accurate as possible by conventional photographic techniques.

BOTANICAL DESCRIPTION OF THE PLANT

The following is a detailed description of the new *Gasteraloe* cultivar named 'D Sigma'. Data was collected in Amposta, Tarragona, Spain from 12 month old plants grown in a glass greenhouse in 5.5 cm. diameter containers. The time of year was Summer and the temperature range was 18-26 degrees Centigrade during the day and 11-21 degrees Centigrade at night. The light level was natural light level. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'D Sigma' has not been tested under all possible conditions and phenotypic differences may be observed with variations in environmental, climatic, and cultural conditions, however, without any variance in genotype.

Botanical classification: *Gasteraloe beguinii* 'D Sigma'.
Annual or perennial: Perennial.
Parentage: The parentage of 'D Sigma' is unknown.
Growth habit: Basal rosette.
Plant shape: Flattened globe shaped.
Suitable container size: 5.5 cm. pots or larger.
Plant height: 8.7 cm.
Plant width: 16.5 cm.
Vigor: Moderate.
Growth rate: Moderate.
Low temperature tolerance: 1° Centigrade.
High temperature tolerance: 40° Centigrade.
Propagation: Leaf cuttings.
Time to initiate roots (summer): 21 days at 20° C.
Time to initiate roots (winter): 35 days at 20° C.
Time to produce a rooted cutting (summer): 170 days at 20° C.
Time to produce a rooted cutting (winter): 180 days at 20° C.
Crop time: Approximately 52 weeks in Amposta, Tarragona, Spain.
Root system: Thick and fleshy.
Plant fragrance: None.
Branching habit: Leaves arise in basal rosette, no branches.
Foliage:

*Leaf arrangement.*—Basal rosette.
*Compound or single.*—Single.
*Quantity of leaves per plant.*—Average 20.
*Leaf shape.*—Narrow triangular to ovate, succulent.
*Leaf aspect.*—Concave across width, flat to slightly curved downward along length.
*Leaf apex.*—Acute with a caudate tip.
*Leaf base.*—Broad cuneate.
*Leaf dimensions.*—8.5 cm. in length, 3.1 cm. in width and 1.0 cm. in thickness.
*Leaf texture* (*upper surface*).—Glabrous.
*Leaf texture* (*lower surface*).—Glabrous.
*Leaf luster* (*upper surface*).—Moderately glossy.
*Leaf luster* (*lower surface*).—Slightly glossy.
*Leaf rugose.*—Not rugose.
*Pubescence.*—Absent.
*Leaf margin.*—Sharp serrate, teeth 0.1 cm. in length and N155A in color.
*Venation pattern.*—None visible.
*Young leaf color* (*upper surface*).—Between NN137A and 147A, fading towards base 145A to 144B, sparsely covered with orbicular pustulate dots, 0.1 cm. in diameter, 192B in color.
*Young leaf color* (*lower surface*).—NN137A, fading towards base 145A to 144B, moderately covered with orbicular dots, 0.1 cm. in diameter, 192B to 192C in color.
*Mature leaf color* (*upper surface*).—Between NN137A and 139A, fading towards base 148D to 191D, moderately pustulate with orbicular dots, 0.1 cm. in diameter, 138C to 138D in color.
*Mature leaf color* (*lower surface*).—Between NN137A and 147A, fading towards base 145B to 145C, densely pustulate with orbicular to oblong dots, 0.1 cm. in diameter, between 138B and 191B in color.

Flower: 'D Sigma' has not produced flowers to date.
Fruit and seed: 'D Sigma' has not produced fruit or seed to date.
Disease and pest resistance: Disease and pest resistance has not been observed.

The invention claimed is:

1. A new and distinct variety of *Gasteraloe* plant named 'D Sigma' as described and illustrated.

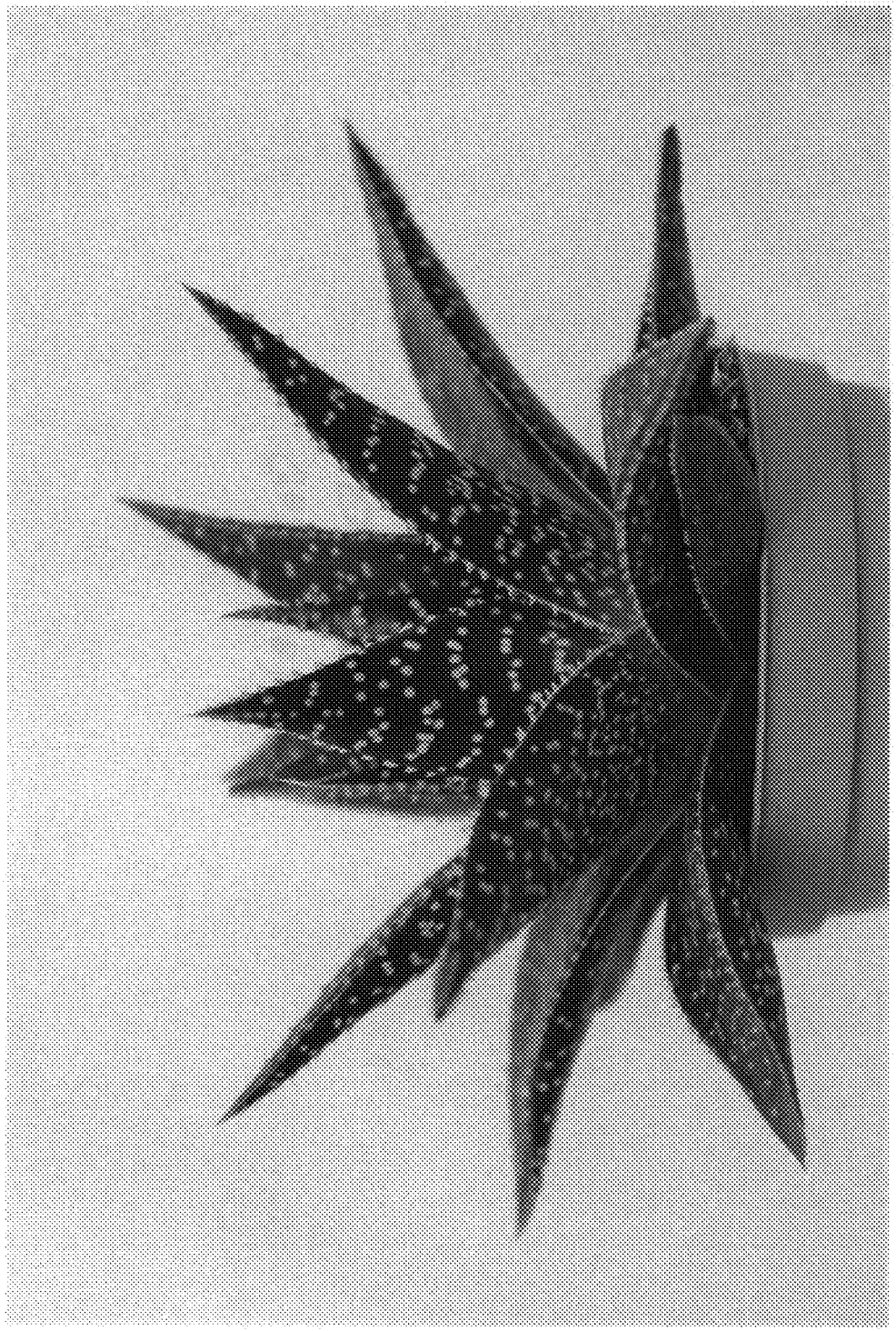

* * * * *